(12) United States Patent
Clark

(10) Patent No.: US 11,458,048 B1
(45) Date of Patent: Oct. 4, 2022

(54) CLOSABLE SANITARY NAPKIN SYSTEM

(71) Applicant: Reynita Clark, St. Thomas, VI (US)

(72) Inventor: Reynita Clark, St. Thomas, VI (US)

(*) Notice: Subject to any disclaimer, the term of this patent is extended or adjusted under 35 U.S.C. 154(b) by 11 days.

(21) Appl. No.: 15/488,022

(22) Filed: Apr. 14, 2017

Related U.S. Application Data

(60) Provisional application No. 62/322,632, filed on Apr. 14, 2016.

(51) Int. Cl.
*A61F 13/551* (2006.01)
*A61F 13/56* (2006.01)
*A61F 13/47* (2006.01)
*A61F 13/84* (2006.01)

(52) U.S. Cl.
CPC .......... *A61F 13/5515* (2013.01); *A61F 13/47* (2013.01); *A61F 13/55135* (2013.01); *A61F 13/5616* (2013.01); *A61F 2013/55195* (2013.01); *A61F 2013/8497* (2013.01)

(58) Field of Classification Search
CPC ................ A61F 13/47; A61F 13/51394; A61F 13/51496; A61F 13/5512; A61F 13/55135; A61F 13/5515; A61F 2013/15243; A61F 2013/51377; A61F 2013/55155; A61F 2013/55195; A61F 2013/8497
See application file for complete search history.

(56) References Cited

U.S. PATENT DOCUMENTS

| | | | | |
|---|---|---|---|---|
| 4,402,689 A * | 9/1983 | Baum | ............... | A61F 13/5515 604/387 |
| 4,781,712 A * | 11/1988 | Barabino | ............ | A61F 13/5514 604/385.201 |
| 4,846,828 A * | 7/1989 | Mendelsohn | ....... | A61F 13/5514 604/387 |
| 4,857,066 A * | 8/1989 | Allison | ................. | A61F 13/551 604/385.13 |
| 5,358,499 A * | 10/1994 | Seidy | .................. | A61F 13/5514 604/385.03 |
| 5,478,336 A * | 12/1995 | Pigneul | ............... | A61F 13/5514 206/438 |
| 9,333,124 B2 * | 5/2016 | Bryant | ..................... | A61L 15/56 |
| 2011/0270210 A1 * | 11/2011 | Rainho das Neves | | A61F 13/5515 604/385.13 |

* cited by examiner

*Primary Examiner* — Catharine L Anderson
(74) *Attorney, Agent, or Firm* — Leavitt Eldredge Law Firm

(57) ABSTRACT

A closable sanitary napkin system that is secured once rolled or closed by flaps attached towards one end. The flaps remain in contact with the bottom of the napkin until the time of disposal when they are pulled out and used to secure the napkin closed. The napkin could also have a pattern or image printed on the bottom surface to obscure any contents of the napkin.

1 Claim, 5 Drawing Sheets

CLOSABLE SANITARY NAPKIN SYSTEM

BACKGROUND

1. Field of the Invention

The present invention relates generally to sanitary napkin systems, and more specifically, to a closeable sanitary napkin system for discreetly and efficiently disposing of a sanitary napkin.

2. Description of Related Art

Sanitary napkin systems are well known in the art and are effective means to absorb discharge. For example, FIGS. 1A, 1B and 1C depict a conventional sanitary napkin system at various stages of use 101 having a napkin 103, fluid 105 and paper 107. During use, the napkin 103 absorbs the fluid 105 and is then removed and wrapped in paper 107 for disposal.

One of the problems commonly associated with system 101 is its excessive waste. For example, it is common to wrap the napkin in excessive quantities of paper to ensure that the napkin does not open during disposal.

Accordingly, although great strides have been made in the area of sanitary napkin systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1A:
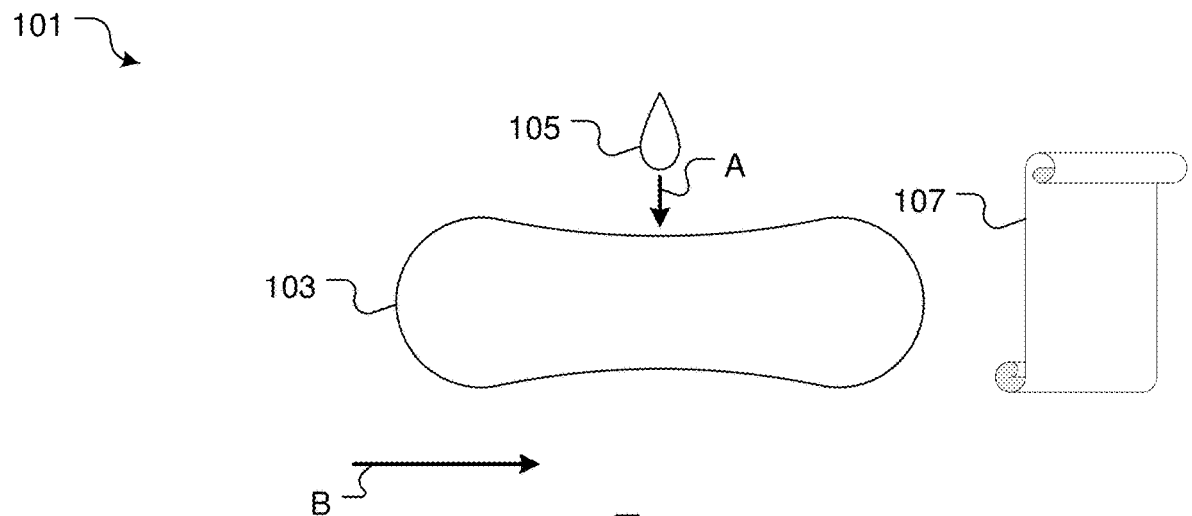
FIGS. 1A, 1B and 1C are side views of a common sanitary napkin system.
Figure 1B:
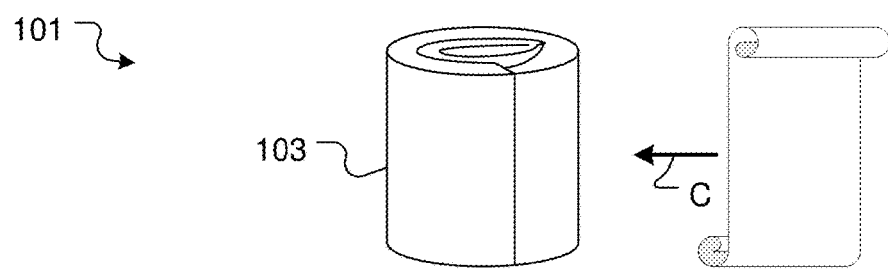
Figure 1C:
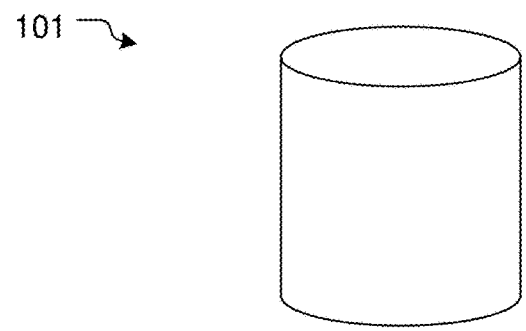

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional sanitary napkin systems. Specifically, the system of the present application provides efficient means of closing the napkin for disposal. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2A:
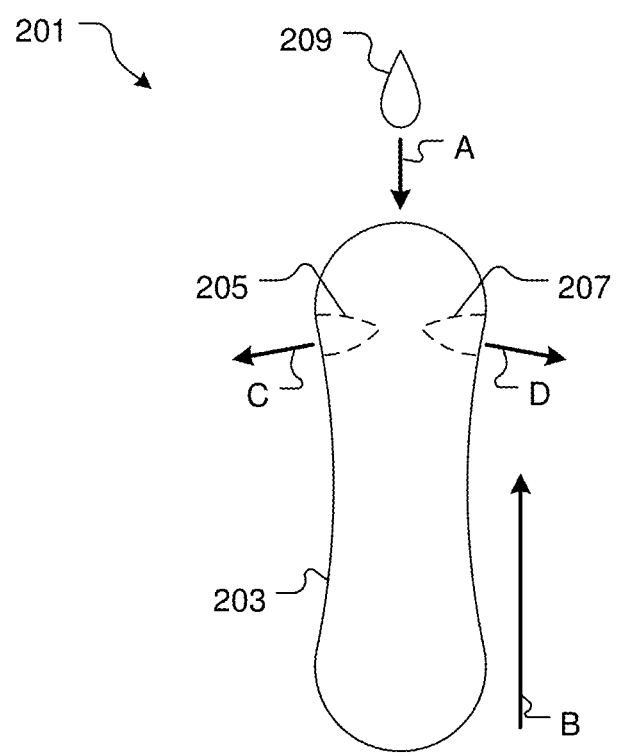
FIGS. 2A, 2B and 2C are top views of a novel closable sanitary napkin system in accordance with a preferred embodiment of the present application.
Figure 2B:
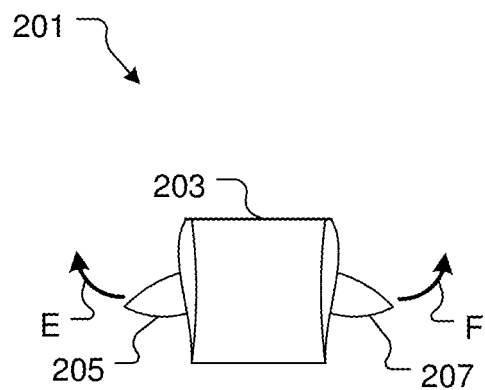
Figure 2C:
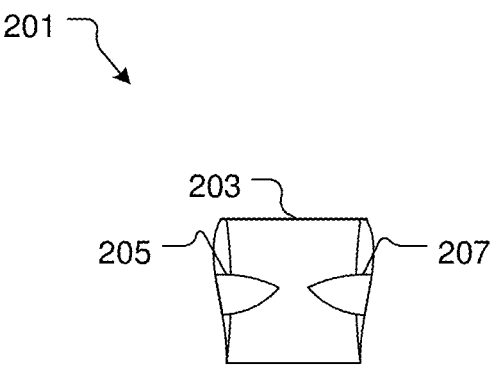

Referring now to the drawings wherein like reference characters identify corresponding or similar elements throughout the several views, FIGS. 2A, 2B and 2C depict top views of a closable sanitary napkin system in accordance with a preferred embodiment of the present application. It will be appreciated that system 201 overcomes one or more of the above-listed problems commonly associated with conventional sanitary napkin systems.

In the contemplated embodiment, system 201 includes a napkin 203 a plurality of flaps 205, 207 flexibly attached towards one end. The napkin 203 is configured to capture a fluid 209.

In use the flaps 205, 207 remain in full contact with the napkin 203 until the fluid 209 has been absorbed by the napkin 203 as depicted by motion A. After the fluid has been absorbed, the napkin 203 is rolled as depicted by motion B. The flaps 205, 207 are opened as depicted by motions C and D respectively. The rolled up napkin 203 is secured in a closed or rolled position by the flaps 205, 207 as depicted by motions E and F and then discarded.

It should be appreciated that one of the unique features believed characteristic of the present application is that flaps 205, 207 allow the napkin 203 to be closed with a minimal amount of material and effort. It will also be appreciate that the flaps 205, 207 could hold the napkin closed by any securing means, such as adhesive, hook and loop, or the like.

Figure 3:
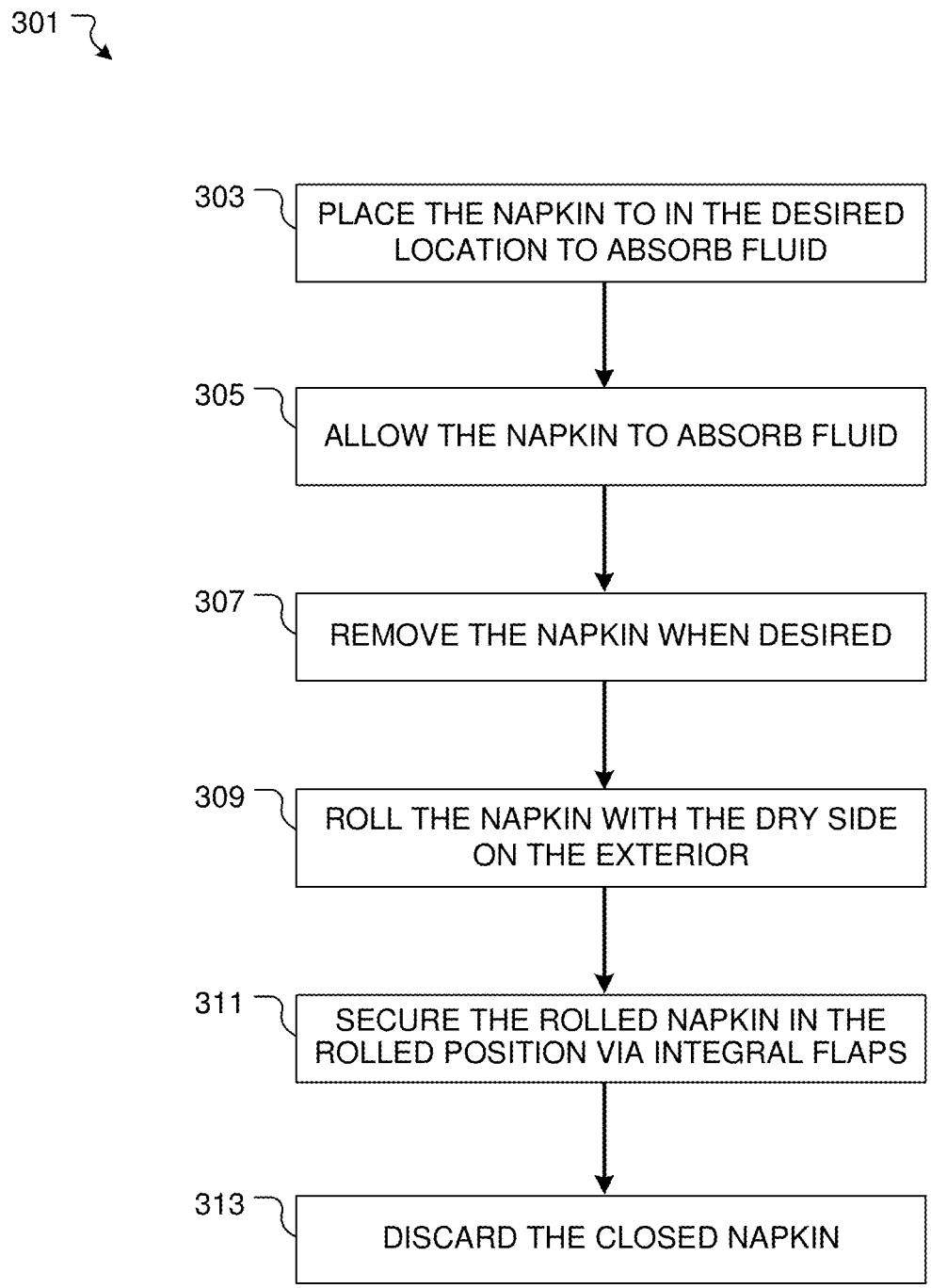
FIG. 3 is a diagram of the method of use of the system of FIGS. 2A, 2B and 2C.

Referring now to FIG. 3 the method of use of the system of the present application is depicted, the method 301 including placing the napkin in the desired location to absorb the fluid 303, allowing the napkin absorb the fluid 305, removing the napkin when desired 309, rolling the napkin 311, securing the rolled napkin in a closed position via the flaps 313 and discarding the closed napkin 315.

Figure 4:
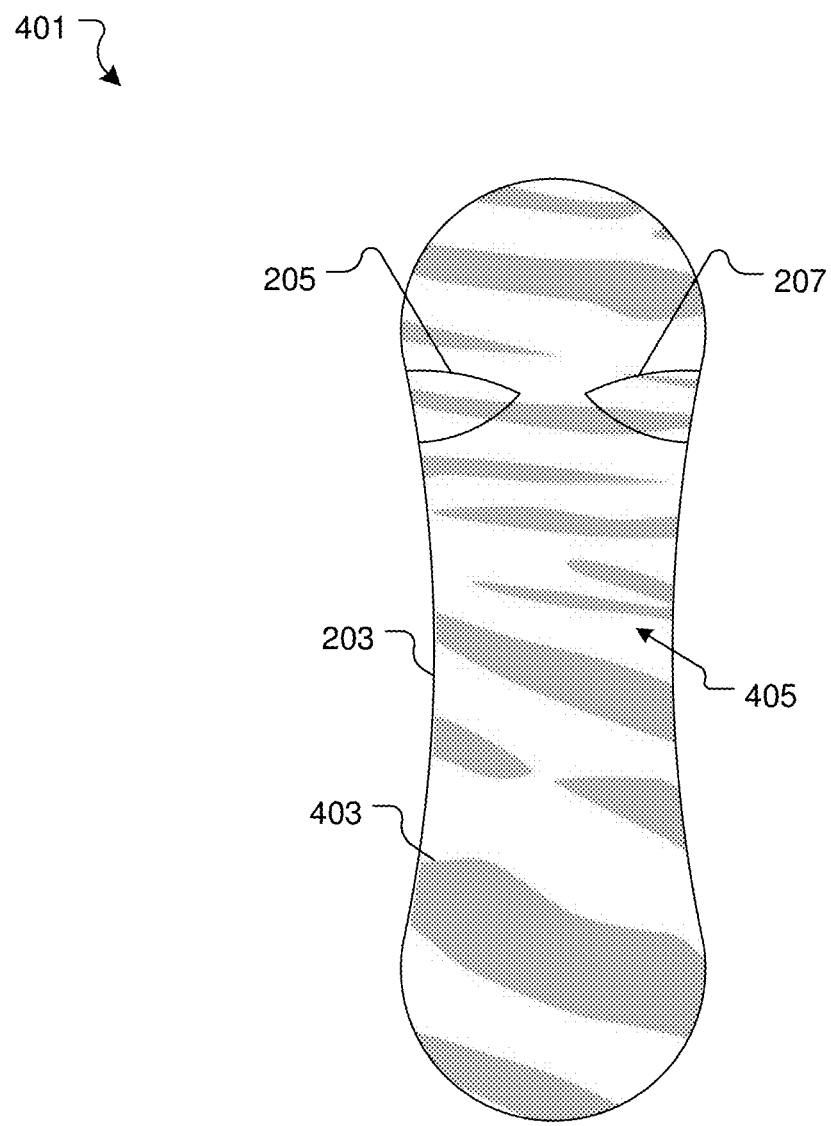
FIG. 4 is a bottom view of an alternative embodiment of the napkin of FIGS. 2A, 2B and 2C.

Referring now to FIG. 4 the bottom view of an alternative embodiment of the system 201 is depicted. The embodiment 401, including the same features and having the same function as system 201 and also including an indicia 403 on the bottom surface 405 of the napkin 203. It will be appreciated that the indicia 403 is both aesthetically pleasing and serves to obscure the contents of the napkin 403.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed:

1. A closable sanitary napkin system comprising:

a napkin having an elongated body with a first side edge and a second side edge, the napkin having a top surface and a bottom surface, the top surface configured to receive fluid;

a first flap flexibly attached to the first side edge such that the first flap is folded behind the bottom surface prior to use, the first flap having an adhesive surface;

a second flap flexibly attached to the second side edge such that the second flap is folded behind the bottom surface prior to use, the second flap having a second adhesive surface;

wherein the first flap and the second flap are attached to the respective first side edge and second side edge at a location wholly above a centerline of the elongated body;

wherein the first flap and the second flap are configured to removably adhere to a bottom surface of the napkin prior to use; and wherein the first flap and the second flap are configured to secure the elongated body in a rolled position after use of the napkin by disengaging with the bottom surface and re-engaging with the bottom surface after the elongated body is rolled.

* * * * *